United States Patent
Bufe et al.

(10) Patent No.: US 8,012,701 B2
(45) Date of Patent: Sep. 6, 2011

(54) AGONISTS OF BITTER TASTE RECEPTORS AND USES THEREOF

(75) Inventors: Bernd Bufe, Ferch (DE); Wolfgang Meyerhof, Norderstedt (DE); Christina Kuhn, Nuthetal (DE)

(73) Assignee: Deutsches Institut fur Ernahrungsforschung Potsdam-Rehbrucke Stiftung des Offentlichen Rechts, Nuthetal (DE)

( * ) Notice: Subject to any disclaimer, the term of this patent is extended or adjusted under 35 U.S.C. 154(b) by 0 days.

(21) Appl. No.: 12/890,897

(22) Filed: Sep. 27, 2010

(65) Prior Publication Data
US 2011/0039757 A1 Feb. 17, 2011

Related U.S. Application Data

(62) Division of application No. 11/791,409, filed as application No. PCT/EP2005/012385 on Nov. 18, 2005, now Pat. No. 7,829,299.

(60) Provisional application No. 60/629,035, filed on Nov. 18, 2004.

(51) Int. Cl.
*G01N 33/566* (2006.01)
*C07K 14/705* (2006.01)

(52) U.S. Cl. .......... 435/7.2; 435/7.1; 435/7.21; 436/501

(58) Field of Classification Search .................. None
See application file for complete search history.

(56) References Cited

U.S. PATENT DOCUMENTS

| 6,558,910 B2 | 5/2003 | Zuker et al. |
| 6,942,874 B2 | 9/2005 | McGregor et al. |
| 7,244,584 B2 | 7/2007 | Zuker et al. |

FOREIGN PATENT DOCUMENTS

| WO | WO 01/18050 | 3/2001 |
| WO | WO 2004/029087 | 4/2004 |

OTHER PUBLICATIONS

Shi, P. et al. "Adaptive Diversification of Bitter Taste Receptor Genes in Mammalian Evolution" *Mol. Biol. Evol.*, 2003, pp. 805-814, vol. 20, No. 5.
Chandrashekar, J. et al. "T2Rs Function as Bitter Taste Receptors" *Cell*, Mar. 17, 2000, pp. 703-711, vol. 100.
Pronin, A. N. et al. "Identification of Ligands for Two Human Bitter T2R Receptors" *Chem. Senses*, 2004, pp. 583-593, vol. 29.
Definition of "conservative substitution" from Dictionary of Cell and Molecular Biology, 3rd Edition, p. 1.
Parry, C. M. et al. "Divergence of T2R chemosensory receptor families in humans, bonobos, and chimpanzees" *PNAS*, Oct. 12, 2004, pp. 14830-14834, vol. 101, No. 41.

*Primary Examiner* — John Ulm
(74) *Attorney, Agent, or Firm* — Saliwanchik, Lloyd & Eisenschenk

(57) ABSTRACT

The present invention relates to agonists of the human bitter-taste receptor hTAS2R3 and its role in bitter taste transduction. The invention also relates to assays for screening molecules that modulate, e.g. suppress or block hTAS2R3 bitter taste transduction or bitter taste response.

Figures 1A, 1B, 1C, 1D:
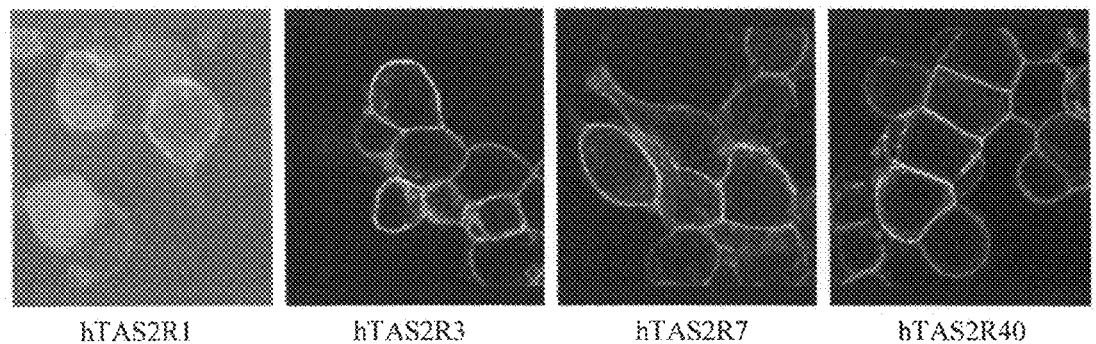

17 Claims, 2 Drawing Sheets
(1 of 2 Drawing Sheet(s) Filed in Color)

hTAS2R1  hTAS2R3  hTAS2R7  hTAS2R40

AGONISTS OF BITTER TASTE RECEPTORS AND USES THEREOF

CROSS-REFERENCE TO RELATED APPLICATIONS

This application is a divisional of U.S. Ser. No. 11/791,409, filed Mar. 11, 2008, which is the U.S. national stage application of International Patent Application No. PCT/EP2005/012385, filed Nov. 18, 2005, which claims the benefit of U.S. Provisional Patent Application No. 60/629,035, filed Nov. 18, 2004, the disclosures of which are hereby incorporated by reference in their entireties, including all figures, tables and amino acid or nucleic acid sequences.

BACKGROUND

Investigators have recently turned their attention to understanding the biological mechanisms of taste, and in particular bitter taste. For a review of the literature see, for example, Caicedo A. and Roper S. D. (2001) Science 291: 1557-1560; Dulac C. (2000) Cell 100: 607-610; Kinnamon S. C. (2000) Neuron 25: 507-510; Lindemann B. (2001) Nature 413: 219-225.; and Margolskee R F. (2001) J. Biol. Chem. 277: 1-4.

Bitter taste is aversive, and as such provides humans with a mechanism of protection against poisonous substances, which are generally bitter-tasting compounds. More subtly, bitter-tastants also affect the palatability of food, beverages, thereby influencing human nutritional habits as is more fully discussed by Drewnowski in "The Science and Complexity of Bitter Taste", (2001) Nutr. Rev. 59: 163-169. They also affect the palatability of other ingestibles such as orally administered pharmaceuticals and nutraceuticals. Understanding the mechanism of bitter taste transduction has implications for the food and pharmaceutical industries. If the bitter taste transduction pathway can be manipulated, it may be possible to suppress or eliminate bitter taste to render foods more palatable and increase patient compliance with oral pharmaceutics.

Taste transduction involves the interaction of molecules, i.e. tastants with taste receptor-expressing cells which reside in the taste buds located in the papillae of the tongue. Taste buds relay information to the brain on the nutrient content of food and the presence of poisons. Recent advances in biochemical and physiological studies have enabled researchers to conclude that bitter taste transduction is mediated by so-called G-protein coupled receptors (GPCRs). GPCRs are 7 transmembrane domain cell surface proteins that amplify signals generated at a cell surface when the receptor interacts with a ligand (a tastant) whereupon they activate heterotrimeric G-proteins. The G-proteins are protein complexes that are composed of alpha and beta-gamma subunits. They are usually referred to by their alpha subunits and classified generally into 4 groups: $G_{alpha\ s,\ i,\ q}$ and $_{12}$. The $G_{alpha\ q}$ type couple with GPCRs to activate phospholipase C which leads to an increase in cellular $Ca^{2+}$. There are many $G_q$-type G-proteins that are promiscuous and can couple to GPCRs, including taste receptors, and these so-called "promiscuous" G-proteins are well known in the art. These G-proteins dissociate into alpha and beta-gamma subunits upon activation, resulting in a complex cascade of cellular events that result in the cell producing second messengers, such as calcium ions, that enable the cells to send a signal to the brain indicating a bitter response.

There is also anatomical evidence that GPCRs mediate bitter taste transduction: clusters of these receptors are found in mammalian taste cells containing gustducin. Gustducin is a G-protein subunit that is implicated in the perception of bitter taste in mammals see, for example, Chandrashekar, J. et al. (2000) Cell 100: 703-711; Matsunami H. et al. (2000) Nature 404: 601-604; or Adler E. et al. (2000) Cell 100: 693-702. cDNAs encoding such GPCRs have been identified, isolated, and used as templates to compare with DNA libraries using in-silico data-mining techniques to identify other related receptors. In this manner it has been possible to identify a family of related receptors, the so-called T2R or TAS2R family of receptors, that have been putatively assigned as bitter receptors.

Humans are able to detect with a limited genetic repertoire of about 30 receptor genes thousands of different bitter compounds. Since their discovery in the year 2000 (Adler E. et al. (2000) supra; Chandrashekar J. et al. (2000) supra; Matsunami H. et al (2000) supra) only few mammalian TAS2Rs have been deorphanised, i.e. ligands, in particular agonists have been identified. The murine mTAS2R5 (Chandrashekar J. et al (2000) supra) and the rat rTAS2R9 (Bufe B. et al. (2002) Nature Genetics 32:397-401) respond to the toxic bitter substance cycloheximide, the mouse mTAS2R8 and the human hTAS2R4 respond to high doses of denatonium and, to a lesser extend, to 6-n-propyl-2-thiouracil (Chandrashekar J. et al. (2000) supra), the human hTAS2R10 and hTAS2R16 respond selectively to strychnine and bitter β-glucopyranosides, respectively (Bufe B. et al. (2002) supra). Although for some TAS2Rs a limited promiscuity (mTAS2R8, hTAS2R4) or specificity for a group of chemically related compounds (hTAS2R16) was reported, the relative selectivity of ligand recognition by the receptors published to date does, by far, not explain the enormous number of bitter tastants recognised by the mammalian gustatory system. There are several possible mechanisms conceivable to increase the number of tastants recognised by a limited number of taste receptor genes, the simplest way would be to have receptors which exhibit a broad tuning to a great number of structurally divergent ligands.

The present inventors now show that the human bitter receptors hTAS2R1 and hTAS2R7 respond to two quite different bitter compounds and, thus, appear to be bitter taste receptors with such a broad tuning. Furthermore, the present inventors were able to show that hTAS2R3 and hTAS2R40 respond specifically to a particular bitter compound and, thus, might constitute examples for more specific bitter taste receptors. This makes the identification of antagonists for the hTAS2R1 and hTAS2R7 receptors particularly attractive, since it can be envisioned that by blocking the hTAS2R1 and/or hTAS2R7 receptor the bitter perception elicited by a wide variety of different bitter tastants can be decreased or blocked. In addition the deorphanization of hTAS2R3 and hTAS2R40 will allow to identify further agonists or antagonists for these particular bitter taste receptors.

DESCRIPTION OF THE INVENTION

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The present inventors have identified agonists for the hTAS2R1, hTAS2R3, hTAS2R7 and hTAS2R40 bitter taste receptors, and have found that they respond with specificity toward certain classes of bitter compounds that are important in the food and pharmaceutical industries. The agonists provided by the present inventors enables the skilled person to design intelligent compound libraries to screen for antagonists to the bitter response of these receptors, which in turn enables the development of compounds and compositions to suppress or eliminate bitter tasting components of foods, in particular animal foods, nutrients and dietary supplements and pharmaceutical or homeopathic preparations containing such phyto-chemicals. Similarly, the invention also enables the skilled person to screen for additional bitter ligands, or even to screen for compounds that enhance a bitter response, such as might be useful in the food industry.

Therefore, in one aspect the present invention provides a method for isolating an agonist or antagonist of hTAS2R1, hTAS2R3, hTAS2R7 and hTAS2R40 bitter taste receptor activity, respectively, wherein the hTAS2R1, hTAS2R3, hTAS2R7 and hTAS2R40 bitter taste receptors are encoded by a polynucleotide selected from the group consisting of:

(a) a polynucleotide encoding at least the mature form of the polypeptide having the deduced amino acid sequence as shown in SEQ ID NO: 2, 4, 6, or 8;

(b) a polynucleotide having the coding sequence, as shown in SEQ ID NO: 1, 3, 5, or 7 encoding at least the mature form of the hTAS2R1, hTAS2R3, hTAS2R7 and hTAS2R40 polypeptide, respectively;

(c) polynucleotides encoding a fragment or derivative of a polypeptide encoded by a polynucleotide of any one of (a) to (b), wherein in said derivative one or more amino acid residues are conservatively substituted compared to said polypeptide, and said fragment or derivative has hTAS2R1, hTAS2R3, hTAS2R7 and hTAS2R40, respectively, bitter taste receptor activity;

(d) polynucleotides which are at least 50% identical to a polynucleotide as defined in any one of (a) to (c) and which code for a polypeptide having hTAS2R1, hTAS2R3, hTAS2R7 and hTAS2R40 bitter taste receptor activity, respectively; and (e) polynucleotides the complementary strand of which hybridizes, preferably under stringent conditions to a polynucleotide as defined in any one of (a) to (d) and which code for a polypeptide having hTAS2R1, hTAS2R3, hTAS2R7 and hTAS2R40 bitter taste receptor activity, respectively;

comprising:
(1) contacting a polypeptide encoded by said polynucleotide, a host cell genetically engineered with said polynucleotide or with a vector containing said polynucleotide with a potential antagonist;
(2) determining whether the potential antagonists antagonizes the bitter taste receptor activity of said polypeptide wherein prior, concomitantly and/or after step (1) said polypeptide, said host cell or said vector is contacted with an agonist selected from the group consisting of chloramphenicol, humulone, and diphenylthiourea, picrotoxinin and yohimbine for hTAS2R1, creatinine for hTAS2R3, creatinine and cromolyn for hTAS2R7 and humulone for hTAS2R40 or agonistic derivatives of the respective agonist thereof.

The polynucleotide employed in this method encodes a polypeptide that still exhibits essentially the same activity as the mature hTAS2R1, hTAS2R3, hTAS2R7 and hTAS2R40 bitter taste receptor, respectively, i.e. has "bitter taste receptor activity". Preferably the polypeptide has at least 20% (e.g., at least: 20%; 30%; 40%; 50%; 60%; 70%; 80%; 90%; 95%; 98%; 99%; 99.5%; or 100% or even more) of the activity of the full-length hTAS2R1, hTAS2R3, hTAS2R7 and hTAS2R40, respectively. One preferred way of measuring hTAS2R1, hTAS2R3, hTAS2R7 and hTAS2R40 activity, respectively, is the ability to release intracellular calcium in a heterologous cell expression system like, for example, (HEK293T/G16gust44) cells that stably expresses a chimeric G-protein consisting of $G_{\alpha 16}$ and 44 carboxylterminal amino acids of α-gustducin, in response to bitter tastants, which is dependent on the expression of polypeptides encoded by the polynucleotides of the present invention. The amount of intracellular calcium released can be monitored by, for example, the in vitro FLIPR assay described herein but also by the measurement of one of a variety of other parameters including, for example, $IP_3$ or cAMP. Additional ways of measuring G-protein coupled receptor activity are known in the art and comprise without limitation electrophysiological methods, transcription assays, which measure, e.g. activation or repression of reporter genes which are coupled to regulatory sequences regulated via the respective G-protein coupled signalling pathway, such reporter proteins comprise, e.g., CAT or LUC; assays measuring internalization of the receptor; or assays in frog melanophore systems, in which pigment movement in melanophores is used as a readout for the activity of adenylate cyclase or phospholipase C (PLC), which in turn are coupled via G-proteins to exogenously expressed receptors (see, for example, McClintock T. S. et al. (1993) Anal. Biochem. 209: 298-305; McClintock T. S. and Lerner M. R. (1997) Brain Res. Brain, Res. Protoc. 2: 59-68, Potenza M N (1992) Pigment Cell Res. 5: 372-328, and Potenza M. N. (1992) Anal. Biochem. 206: 315-322)

The term "potential antagonist", comprises any perceivable chemical substance or combination thereof in a non-purified, partially purified or purified state, however, an antagonist of hTAS2R1, hTAS2R3, hTAS2R7 and hTAS2R40 bitter taste receptor activity, respectively, is a substance which lowers the hTAS2R1, hTAS2R3, hTAS2R7 and hTAS2R40 bitter taste receptor activity, respectively, determined in the presence of the respective agonist by at least 10% (e.g., at least: 10%, 15%; 20%; 30%; 40%; 50%; 60%; 70%; 80%; 90%; 95%; 98%; 99%; 99.5%; or 100%) once contacted with the bitter taste receptor. Preferably the antagonist exerts this action when it is contacted prior, concomitantly or after, preferably concomitantly, the contacting the hTAS2R1, hTAS2R3, hTAS2R7 and hTAS2R40 polypeptide, respectively, the host cell expressing the hTAS2R1, hTAS2R3, hTAS2R7 and hTAS2R40 polypeptide, respectively, or the vector comprising the hTAS2R1, hTAS2R3, hTAS2R7 and hTAS2R40 polypeptide, respectively, with one of the identified hTAS2R1, hTASR3, hTASR7 and hTASR40 agonists, respectively.

The hTAS2R1, hTAS2R3, hTAS2R7 and hTAS2R40 polynucleotide molecules, respectively, usable in the method of the present invention can be DNA, cDNA, genomic DNA, synthetic DNA, or RNA, and can be double-stranded or single-stranded, the sense and/or an antisense strand. Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription.

The polynucleotide molecules useable in the method of the present invention can contain naturally occurring sequences, or sequences that differ from those that occur naturally, but, due to the degeneracy of the genetic code, encode the same polypeptide (for example, the polypeptide with SEQ ID NO:

2, 4, 6, or 8). In addition, these nucleic acid molecules are not limited to coding sequences, e.g., they can include some or all of the non-coding sequences that lie upstream or downstream from a coding sequence.

The polynucleotide molecules of the invention can be synthesized in vitro (for example, by phosphoramidite-based synthesis) or obtained from a cell, such as the cell of a bacteria or a mammal. The nucleic acids can be those of a human but also derived from a non-human primate, mouse, rat, guinea pig, cow, sheep, horse, pig, rabbit, dog, or cat as long as they fulfill the criteria set out above. Combinations or modifications of the nucleotides within these types of nucleic acids are also encompassed.

In addition, the polynucleotides useable in the method of the present invention can encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

In certain preferred embodiments the method of the present invention uses isolated nucleic acid molecules which are at least 50% (or 55%, 65%, 75%, 85%/a, 95%, or 98%) identical to: (a) a nucleic acid molecule that encodes the polypeptide of SEQ ID NO: 2, 4, 6 or 8; (b) the nucleotide sequence of SEQ ID NO: 1, 3, 5, or 7 and (c) a nucleic acid molecule which includes a segment of at least 30 (e.g., at least 30, 40, 50, 60, 80, 100, 125, 150, 175, 200, 250, 300, 400, 500, 600, 700, 800, 850, and 900) nucleotides of SEQ ID NO: 1, 3, 5 and 7, respectively.

The determination of percent identity between two sequences is accomplished using the mathematical algorithm of Karlin and Altschul (1993) *Proc. Natl. Acad. Sci. USA* 90: 5873-5877. Such an algorithm is incorporated into the BLASTN and BLASTP programs of Altschul et al. (1990) J. Mol. Biol. 215: 403-410. BLAST nucleotide searches are performed with the BLASTN program, score=100, word length=12, to obtain nucleotide sequences homologous to hTAS2R1, hTAS2R3, hTAS2R7 or hTAS2R40 encoding nucleic acids. BLAST protein searches are performed with the BLASTP program, score=50, wordlength=3, to obtain amino acid sequences homologous to the hTAS2R1, hTAS2R3, hTAS2R7 and hTAS2R40 polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

Hybridization can also be used as a measure of homology between two nucleic acid sequences. A nucleic acid sequence encoding hTAS2R1, hTAS2R3, hTAS2R7 or hTAS2R40, or a portion thereof, can be used as a hybridization probe according to standard hybridization techniques. The hybridization of a hTAS2R1, hTAS2R3, hTAS2R7 or hTAS2R40 probe to DNA or RNA from a test source (e.g., a mammalian cell) is an indication of the presence of the hTAS2R1, hTAS2R3, hTAS2R7 or hTAS2R40 DNA or RNA in the test source. Hybridization conditions are known to those skilled in the art and can be found, for example, in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The polynucleotides or proteins useable in the method of the present invention can be comprised in a vector containing the polynucleotide(s) or a protein encoded by above-mentioned polynucleotide. The term "vector" refers to a protein or a polynucleotide or a mixture thereof which is capable of being introduced or of introducing the proteins and/or nucleic acid comprised therein into a cell. It is preferred that the proteins encoded by the introduced polynucleotide are expressed within the cell upon introduction of the vector.

In a preferred embodiment a vector useable in the method of the present invention comprises plasmids, phagemids, phages, cosmids, artificial mammalian chromosomes, knock-out or knock-in constructs, viruses, in particular adenoviruses, vaccinia viruses, attenuated vaccinia viruses, canary pox viruses, lentivirus (Chang, L. J. and Gay, E. E. (2001) Curr. Gene Therap. 1: 237-251), herpes viruses, in particular Herpes simplex virus (HSV-1, Carlezon, W. A. et al. (2000) Crit. Rev. Neurobiol. 14: 47-67), baculovirus, retrovirus, adeno-associated-virus (AAV, Carter, P. J. and Samulski, R. J. (2000) J. Mol. Med. 6:17-27), rhinovirus, human immune deficiency virus (HIV), filovirus and engineered versions thereof (see, for example, Cobinger G. P. et al. (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3: 466-76 and Springer et al. (1998) Mol. Cell. 2: 549-58). Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1, 2-Dioleyloxpropyl-3-trimethylammoniumbromid) and DPOE (Dioleoylphosphatidyl-ethanolamin) which both have been used on a variety of cell lines.

Nucleic acid coated particles are another means for the introduction of nucleic acids into cells using so called "gene guns", which allow the mechanical introduction of particles into cells. Preferably the particles itself are inert, and therefore, are in a preferred embodiment made out of gold spheres.

In a further aspect polynucleotides useable in the method of the present invention are operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression like, for example, promoters transcribed by RNA polymerase III like, e.g. promoters for the snRNA U6 or scRNA 7SK gene, the cytomegalovirus hCMV immediate early gene, the early or late promoters of SV40 adenovirus, viral promoter and activator sequences derived from, e.g. NBV, HCV, HSV, HPV, EBV, HTLV, MMTV or HIV; which allow inducible expression like, for example, CUP-1 promoter, the tet-repressor as employed, for example, in the tet-on or tet-off systems, the lac system, the trp system; regulatory elements directing tissue specific expression, preferably taste bud specific expression, e.g. PLCβ2 promoter or gustducin promoter, regulatory elements directing cell cycle specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or α-mating factors.

As used herein, "operatively linked" means incorporated into a genetic construct so that expression control sequences effectively control expression of a coding sequence of interest.

Similarly, the polynucleotides useable in the method of the present invention can form part of a hybrid gene encoding additional polypeptide sequences, for example, a sequence that functions as a marker or reporter. Examples of marker and reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the method of the invention, skilled artisans will be aware of additional useful reagents, for example, additional sequences that can serve the function of a marker or reporter.

The method of the present invention may also use hybrid polypeptides or polynucleotides encoding them. In general a hybrid polypeptide will include a first portion and a second portion; the first portion being one or more hTAS2R1, hTAS2R3, hTAS2R7 or hTAS2R40 polypeptide and the second portion being, for example, the reporter(s) described above or an Ig constant region or part of an Ig constant region, e.g., the CH2 and CH3 domains of IgG2a heavy chain. Other hybrids could include an antigenic tag or His tag to facilitate purification and/or detection. Recombinant nucleic acid molecules can also contain a polynucleotide sequence encoding the hTAS2R1, hTAS2R3, hTAS2R7 or hTAS2R40 polypeptide operatively linked to a heterologous signal sequence. Such signal sequences can direct the protein to different compartments within the cell and are well known to someone of skill in the art. A preferred signal sequence is a sequence that facilitates secretion of the resulting protein.

Another aspect of the present invention is the use of a host cell genetically engineered with a polynucleotide or a vector as outlined above. The host cells that may be used in the method of the present invention include but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 or Hi5 cells, which can be infected with, for example, recombinant virus expression vectors (for example, baculovirus) containing the polynucleotide molecules; Xenopus oocytes, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing a hTAS2R1, hTAS2R3, hTAS2R7 or hTAS2R40 nucleotide sequence; or mammalian cell systems (for example, COS, CHO, BHK, HEK293, VERO, HeLa, MDCK, Wi38, and NIH 3T3 cells), which can be transformed with recombinant expression constructs containing, for example, promoters derived, for example, from the genome of mammalian cells (for example, the metallothionein promoter) from mammalian viruses (for example, the adenovirus late promoter and the vaccinia virus 7.5K promoter) or from bacterial cells (for example, the tet-repressor binding is employed in the tet-on and tet-off systems). Also useful as host cells are primary or secondary cells obtained directly from a mammal and transfected with a plasmid vector or infected with a viral vector. Depending on the host cell and the respective vector used to introduce the polynucleotide of the invention the polynucleotide can integrate, for example, into the chromosome or the mitochondrial DNA or can be maintained extrachromosomally like, for example, episomally or can be only transiently comprised in the cells.

In a preferred embodiment, the hTAS2R1, hTAS2R3, hTAS2R7 or hTAS2R40 expressed by such cells are functional and have bitter taste receptor activity, i.e., upon binding to one or more bitter molecules they trigger an activation pathway in the cell. The cells are preferably mammalian (e.g., human, non-human primate, horse, bovine, sheep, pig, dog, cat, goat, rabbit, mouse, rat, guinea pig, hamster, or gerbil) cells, insect cells, bacterial cells, or fungal (including yeast) cells.

The polypeptides useable in the method of the invention include all those disclosed herein and functional fragments of these polypeptides. The terms "polypeptide" and "protein" are used interchangeably and mean any peptide-linked chain of amino acids, regardless of length or posttranslational modification. As used herein, a functional fragment of the hTAS2R1, hTAS2R3, hTAS2R7 or hTAS2R40 is a fragment of the hTAS2R1, hTAS2R3, hTAS2R7 or hTAS2R40 that is shorter than the full-length hTAS2R1, hTASR3, hTASR7 or hTASR40 but that has at least 20% (e.g., at least: 20%; 30%; 40%; 50%; 60%; 70%; 80%; 90%; 95%; 98%; 99%; 99.5%; or 100% or even more) of the ability of the full-length hTAS2R1, hTAS2R3, hTAS2R7 or hTAS2R40 to be stimulated by one of the bitter substances identified herein. Binding assays and bitter substances are described in more detail herein below. The polypeptides can also include fusion proteins that contain either a full-length hTAS2R1, hTAS2R3, hTAS2R7 or hTAS2R40 polypeptide or a functional fragment of it fused to an unrelated amino acid sequence. The unrelated sequences can add further functional domains or signal peptides.

The polypeptides can be any of those described above but with not more than 50 (e.g., not more than: 50, 45, 40, 35, 30, 25, 20, 15, 14, 13, 12, 11, 10, nine, eight, seven, six, five, four, three, two, or one) conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required of a polypeptide having one or more conservative substitutions is that it has at least 20% (e.g., at least: 20%; 30%; 40%; 50%; 60%; 70%; 80%; 90%; 95%; 98%; 99%; 99.5%; or 100% or even more) of the ability of the full-length hTAS2R1, hTAS2R3, hTAS2R7 or hTAS2R40 to be stimulated by the respective bitter substance.

Polypeptides and fragments of the polypeptides useable in the method of the present invention can be modified, for example, for in vivo use by the addition of blocking agents, at the amino- and/or carboxyl-terminal ends, to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

The antagonists or agonists of the bitter taste receptors identified herein are of great importance for specific stimulation of a given bitter taste receptor and identification of substances that antagonize it, respectively.

The term "contacting" in the context of the present invention means any interaction between the antagonist and/or agonist with the polypeptide or the host cell, whereby any of the at least two components can be independently of each other in a liquid phase, for example in solution, or in suspension or can be bound to a solid phase, for example, in the form of an essentially planar surface or in the form of particles, pearls or the like. In a preferred embodiment a multitude of different compounds are immobilized on a solid surface like, for example, on a compound library chip and the protein of the present invention is subsequently contacted with such a chip. In another preferred embodiment the host cells are genetically engineered with a polynucleotide encoding hTAS2R1, hTAS2R3, hTAS2R7 or hTAS2R40 or with a vector containing such a polynucleotide, express the hTAS2R1, hTAS2R3, hTAS2R7 or hTAS2R40 bitter taste receptor at the cell surface and are contacted separately in small containers, e.g., microtitre plates, with various compounds.

The term "agonistic derivatives thereof" refers to agonists, which are derived from the respectively indicated agonist, i.e. bitter substance, by chemical modification and which elicit at least 20% (e.g., at least: 20%; 30%; 40%; 50%; 60%; 70%; 80%; 90%; 95%; 98%; 99%; 99.5%; or 100% or even more) of the bitter taste receptor activity, if compared to the respective unmodified bitter substance. Chemical modification includes without limitation the introduction of one or more, preferably two, three or four novel side chains or residues or the exchange of one or more functional groups like, for example, introduction or exchange of H; linear or branched alkyl, in particular lower alkyl ($C_1$, $C_2$, $C_3$, $C_4$, and $C_5$, e.g. methyl, ethyl, n-propyl, isopropyl, n-butyl, isobutyl, tert-butyl, n-pentyl or iso-pentyl); substituted linear or branched alkyl, in particular lower substituted alkyl; linear or branched alkenyl, in particular lower alkenyl ($C_2$, $C_3$, $C_4$ and $C_5$, e.g. ethenyl, 1-propenyl, 2-propenyl, iso-propenyl, 1-butenyl, 2-butenyl, 3-butenyl; substituted linear or branched alkenyl, in particular lower substituted alkenyl; linear or branched alkinyl, in particular lower alkinyl ($C_2$, $C_3$, $C_4$ and $C_5$); substituted linear or branched alkinyl, in particular lower substituted alkinyl; linear or branched alkanol, in particular lower alkanol ($C_2$, $C_3$, $C_4$, and $C_5$); linear or branched alkanal, in particular lower alkanal ($C_1$, $C_2$, $C_3$, $C_4$, and $C_5$, e.g. COH, $CH_2COH$, $CH_2CH_2COH$; linear or branched alkyl carboxyl group, in particular lower alkyl carboxyl group ($C_1$, $C_2$, $C_3$, $C_4$ and $C_5$, e.g. formic, acetic, propionic, butyric, pentanoic acid group); substituted linear or branched alkyl carboxyl groups, in particular lower alkyl carboxyl group ($C_2$, $C_3$, $C_4$ and $C_5$, e.g. 2-methyl acetic acid, acetic acid, propionic acid, butyric acid, pentanoic acid group); aryl, in particular phenyl; substituted aryl, in particular substituted aryl; heteroaryl; substituted heteroaryl; alkylaryl, in particular benzyl; substituted alkylaryl; in particular substituted benzyl; alkylheteroaryl; substituted alkylheteroaryl; aminoalkyl, $C_1$, $C_2$, $C_3$, $C_4$ and $C_5$, e.g. —$NHCH_3$, —$NHCH_2CH_3$, —$N(CH_3)_2$; substituted aminoalkyl; aminoketone, in particular —NH-$COCH_3$; substituted aminoketone; aminoaryl; in particular —NH-Ph; substituted aminoaryl, in particular substituted —NH-Ph; CN; $NH_2$; Halogen, in particular F, Cl, and Br; $NO_2$; OH; SH; NH; CN; or COOH group. If the residues mentioned above are substituted they are preferably mono, di, or tri substituted with a substituent selected from the group of halogen, in particular F, Cl, and Br, $NH_2$, $NO_2$, OH, SH, NH, CN, aryl, alkylaryl, heteroaryl, alkylheteroaryl, COH or COOH. The various chemically modified agonists can be assessed for their activity in any of the assay systems described herein.

As a further step after measuring the antagonizing effect of a potential antagonist and after having measured the decrease of bitter taste for at least two different potential antagonists at least one potential antagonist can be selected, for example, on grounds of the detected decrease of intracellular release of calcium, if compared to contacting with the known agonist alone.

The thus selected (potential) antagonist is than in a preferred embodiment modified in a further step. Modification can be effected by a variety of methods known in the art, which include without limitation the introduction of one or more, preferably two, three or four novel side chains or residues or the exchange of one or more functional groups like, for example, introduction or exchange of halogens, in particular F, Cl or Br; the introduction or exchange of lower alkyl residues, preferably having one to five carbon atoms like, for example, methyl, ethyl, n-propyl, isopropyl, n-butyl, isobutyl, tert-butyl, n-pentyl or iso-pentyl residues; lower alkenyl residues, preferably having two, three, four or five carbon atoms; lower alkinyl residues, preferably having two, three, four or five carbon atoms, which can in a preferred embodiment be further substituted with F, Cl, Br, $NH_2$, $NO_2$, OH, SH, NH, CN, aryl, heteroaryl, COH or COOH group; or the introduction of, for example, one or more residue(s) selected from the group consisting of $NH_2$, $NO_2$, OH, SH, NH, CN, aryl, alkylaryl, heteroaryl, alkylheteroaryl, COH or COOH group.

The thus modified (potential) antagonists are than individually tested with the method of the present invention, i.e. they are contacted with the polypeptide as such or with the polypeptide expressed in a host cell, which has been contacted prior, concomitantly or after step (1) with one of the indentified agonists or derivatives thereof and subsequently activation of the bitter taste receptor activity by the modified antagonists is measured. The activation of the hTAS2R1, hTAS2R3, hTAS2R7 or hTAS2R40 protein can be measured, e.g. by the intracellular calcium release mediated. If needed the steps of selecting the antagonist, modifying the compound, contacting the antagonist with a polypeptide or a host cell and measuring of the activation of the bitter taste receptor activity can be repeated a third or any given number of times as required. The above described method is also termed "directed evolution" of an antagonist since it involves a multitude of steps including modification and selection, whereby antagonizing or agonizing compounds are selected in an "evolutionary" process optimizing their capabilities with respect to a particular property, e.g. their ability to inhibit, activate or modulate the activity of hTAS2R1, hTAS2R3, hTAS2R7 or hTAS2R40, in particular inhibit or stimulate the intracellular release of calcium.

In order to express cDNAs encoding the receptors, one typically subclones receptor cDNA into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available. The eukaryotic expression vector may be, for example an adenoviral vector, an adeno-associated vector, or a retroviral vector.

In addition to the promoter, the expression vector typically contains a transcription unit or expression cassette that contains all the additional elements required for the expression of the receptor-encoding nucleic acid in host cells. A typical expression cassette thus contains a promoter operatively linked to the nucleic acid sequence encoding the receptor and signals required for efficient polyadenylation of the transcript, ribosome binding sites, and translation termination. The nucleic acid sequence encoding the receptor may typically be linked to a membrane-targeting signal such as the N-terminal 45 amino acids of the rat somatostatin receptor 3 sequence to promote efficient cell-surface expression of the recombinant receptor. Additional elements of the cassette may include, for example enhancers.

An expression cassette should also contain a transcription termination region down-stream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g. SV40 vectors, papilloma virus vectors, and vectors derived from Epstein-Barr virus. Other exemplary eukaryotic vectors include pMSG, pAV009/A+, pMT010/A+, pMAMneo-5, baculovirus pDSVE, pcDNA3.1, pIRES and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that are typically included in expression vectors also include a replicon that functions in *E. coli*, a gene encoding drug resistance to permit selection of bacteria that harbor recombinant plasmids, and unique restriction sites in nonessential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines that express large quantities of the receptor, which are then purified using standard techniques.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing the receptor.

After the expression vector is introduced into the cells, the transfected cells may be cultured under conditions favouring expression of the receptor, which is recovered from the culture using standard techniques. For example the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

The activity of the receptor described herein can be assessed using a variety of in vitro and in vivo assays to determine functional, chemical, and physical effects, e.g., measuring ligand binding, secondary messengers (e.g., cAMP, cGMP, $IP_3$, DAG, or $Ca^{2+}$) ion flux, phosphorylation levels, transcription levels, of reporter constructs neurotransmitter levels, and the like. Such assays are used in the method of the present invention to test for the activity of the receptors.

Samples or assays that are treated with a potential receptor agonist may be compared to control samples without the test compound (agonist or antagonist), to examine the extent of modulation. Control samples (treated with agonists only) are assigned a relative receptor activity value of 100. Inhibition of receptor activity is achieved when the receptor activity value relative to the control is lower, and conversely receptor activity is enhanced when activity relative to the control is higher in the presence of identical amounts of the respective agonist.

The effects of the test compounds upon the function of the receptors can be measured by examining any of the parameters described above. Any suitable physiological change that affects receptor activity can be used to assess the influence of a test compound on the receptors of this invention. When the functional consequences are determined using intact cells or animals, one can measure a variety of effects such as changes in intracellular secondary messengers such as $Ca^{2+}$, $IP_3$ or cAMP.

Preferred assays for G-protein coupled receptors include cells that are loaded with ion sensitive dyes to report receptor activity. In assays for identifying modulatory compounds, changes in the level of ions in the cytoplasm or membrane voltage will be monitored using an ion sensitive or membrane voltage fluorescent indicator, respectively. For G-protein coupled receptors, promiscuous G-proteins such as $G_{\alpha 15}$ and $G_{\alpha 16}$ and chimeric G-proteins can be used in the assay of choice (see, for example, Wilkie et al. (1991) Proc. Nat. Acad. Sci. USA 88: 10049-10053). Such promiscuous G-proteins allow coupling of a wide range of receptors to G-protein dependent signal pathways.

Receptor activation typically initiates subsequent intracellular events, e.g. increases in second messengers such as $IP_3$, which releases intracellular stores of calcium ions. Activation of some G-protein coupled receptors stimulates the formation of inositol trisphosphate through phospholipase C-mediated hydrolysis of phosphatidylinositol bisphosphate (Berridge & Irvine (1984) Nature 312: 315-21). $IP_3$ in turn stimulates the release of intracellular calcium ion stores. Thus, a change in cytoplasmic calcium ion levels, or a change in second messenger levels such as $IP_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EGTA, to distinguish fluorescence response resulting from calcium release from internal stores.

In a preferred embodiment, receptor activity is measured by expressing the hTAS2R1, hTAS2R3, hTAS2R7, or hTAS2R40 receptors in a heterologous cell with a promiscuous G-protein, such as $G_{\alpha15}$, $G_{\alpha16}$, or a chimeric G-protein that links the receptor to a phospholipase C signal transduction pathway. A preferred cell line is HEK-293, although other mammalian cell lines are also preferred such as CHO and COS cells. Modulation of taste transduction is assayed by measuring changes in intracellular $Ca^{2+}$ levels, which change in response to modulation of the receptor signal transduction pathway via administration of a molecule that associates with the receptor. Changes in $Ca^{2+}$ levels are optionally measured using fluorescent $Ca^{2+}$ indicator dyes and fluorometric imaging.

The activity of the signalling molecule and the increase or decrease of that activity in response to the potential agonist or antagonist can be determined as outlined above with respect to the identification of bitter receptor taste activity. The respectively indicated percent increases or decreases of the activity, which are required to qualify as antagonist or agonist do apply mutatis mutandis. Additionally the term "contacting" has the meaning as outlined above. Preferably the signalling molecule and/or the promiscuous G-protein has been introduced into the cell. The types of cell lines, which are preferred are those indicated above.

In yet another embodiment, the ligand-binding domains of the receptors can be employed in vitro in soluble or solid-state reactions to assay for ligand binding. Ligand binding to a receptor, or a domain of a receptor, can be tested in solution, in a bilayer membrane attached to a solid phase, in a lipid monolayer or vesicles. Thereby, the binding of a modulator to the receptor, or domain, can be observed using changes in spectroscopic characteristics, e.g. fluorescence, absorbance or refractive index; or hydrodynamic (e.g. shape), chromatographic, or solubility properties, as is generally known in the art.

The compounds tested as modulators of the receptors can be any small chemical compound, or a biological entity, such as a protein, sugar, nucleic acid or lipid. Typically, test compounds will be small chemical molecules. Essentially any chemical compound can be used as a potential modulator or ligand in the assays of the invention, although knowledge of the ligand specificity of an individual receptor would enable the skilled person to make an intelligent selection of interesting compounds. The assays may be designed to screen large chemical libraries by automating the assay steps and providing compounds from any convenient source to assays, which are typically run in parallel (e.g., in microtiter formats on microtiter plates in robotic assays). The skilled person will understand that there are many suppliers of libraries of chemical compounds.

Assays may be run in high throughput screening methods that involve providing a combinatorial chemical or peptide library containing a large number of potential therapeutic, or tastant compounds (that are potential ligand compounds). Such libraries are then screened in one or more assays, as described herein, to identify those library members (particular chemical species or subclasses) that display a desired characteristic activity. The compounds thus identified can serve as lead compounds to further develop modulators for final products, or can themselves be used as actual modulators.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art and no more needs to be stated here.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds is possible using the integrated systems of the invention.

Antagonists found by assay technology herein above described, or development compounds formed from such antagonists can be administered directly to a human subject to modulate bitter taste. Alternatively, such compounds can be formulated with other ingredients of preparations to be taken orally, for example, foods, including animal food, and beverages, pharmaceutical or nutraceutical or homeopathic preparations.

Therefore, another aspect of the invention is a process for the production of foodstuffs or any precursor material or additive employed in the production of foodstuffs comprising the steps of the above described processes for the identification of an antagonist of hTAS2R1, hTAS2R3, hTAS2R7 or hTAS2R40 and the subsequent step of admixing the identified antagonist with foodstuffs or any precursor material or additive employed in the production of foodstuffs.

Bitter taste is a particular problem when orally administering pharmaceuticals, which often have an unpleasant bitter taste. In particular in elderly persons, children and chronically ill patients this taste can lead to a lack of complinace with a treatment regimen. In addition in veterinary applications the oral administration of bitter tasting pharmaceuticals can be problematic. Therefore, a further aspect of the invention is a process for the production of a nutraceutical or pharmaceutical composition comprising the step of the process to identify an antagonist or an agonist of hTAS2R1, hTAS2R3, hTAS2R7 and hTAS2R40 and the subsequent step of formulating the antagonist with an active agent in a pharmaceutically acceptable form.

Consequently, a further aspect of the invention is a foodstuff, in particular animal food, or any precursor material or additive employed in the production of foodstuffs produced according to the method of the invention.

Also comprised is a nutraceutical or pharmaceutical composition produced according to the method of the invention and at least one active agent and optionally a pharmaceutically acceptable carrier and/or adjuvants.

The amount of compound to be taken orally must be sufficient to affect a beneficial response in the human subject, and will be determined by the efficacy of the particular taste modulators and the existence, nature, and extent of any adverse side-effects that accompany the administration of a particular compound.

A further aspect of the present invention is the use of an agonist of hTAS2R1, hTAS2R3, hTAS2R7 or hTAS2R40 activity selected from the group consisting of chloramphenicol, humulone, diphenylthiourea, picrotoxinin and yohimbine for hTAS2R1, creatinine for hTAS2R3, creatinine and cromolyn for hTAS2R7 and humulone for hTAS2R40 and agonistic derivatives thereof to enhance bitter taste.

A further aspect of the present invention is the use of an antagonist of hTAS2R1, hTAS2R3, hTAS2R7 and hTAS2R40 activity selected from the group of antagonistic derivatives of chloramphenicol, humulone, diphenylthiourea, picrotoxinin and yohimbine for hTAS2R1, creatinine for hTAS2R3, creatinine and cromolyn for hTAS2R7 and humulone for hTAS2R40 to suppress bitter taste.

The term "antagonistic derivatives" of the respectively bitter tastant is a substance, which is derived from the respectively indicated agonist, i.e. bitter substance, by chemical modification and which lowers the hTAS2R1, hTAS2R3, hTAS2R7 and hTAS2R40 bitter taste receptor activity, respectively, determined in the presence of the respective agonist, by at least 10% (e.g. at least 10%, 15%, 20%, 30%, 40%, 50%, 60%, 70%, 80%, 90%, 95%, 98%, 99%, 99.5% or 100%) once contacted with a bitter taste receptor. Preferably the antagonistic derivative exerts this action, when it is contacted prior, concomitantly or after, preferably concomitantly, to the contacting of the hTAS2R1, hTAS2R3, hTAS2R7 and hTAS2R40 polypeptide, respectively, the host cell expressing the hTAS2R1, hTAS2R3, hTAS2R7 and hTAS2R40 polypeptide, respectively, or the vector comprising the hTAS2R1, hTAS2R3, hTAS2R7 and hTAS2R40 polypeptide, respectively with the agonist.

Chemical modification includes without limitation the introduction of one or more, preferably two, three or four novel side chains or residues or the exchange of one or more functional groups like, for example, introduction or exchange of H; linear or branched alkyl, in particular lower alkyl ($C_1$, $C_2$, $C_3$, $C_4$, and $C_5$, e.g. methyl, ethyl, n-propyl, isopropyl, n-butyl, isobutyl, tert-butyl, n-pentyl or iso-pentyl); substituted linear or branched alkyl, in particular lower substituted alkyl; linear or branched alkenyl, in particular lower alkenyl ($C_2$, $C_3$, $C_4$ and $C_5$, e.g. ethenyl, 1-propenyl, 2-propenyl, iso-propenyl, 1-butenyl, 2-butenyl, 3-butenyl; substituted linear or branched alkenyl, in particular lower substituted alkenyl; linear or branched alkynyl, in particular lower alkynyl ($C_2$, $C_3$, $C_4$ and $C_5$); substituted linear or branched alkynyl, in particular lower substituted alkinyl; linear or branched alkanol, in particular lower alkanol ($C_2$, $C_3$, $C_4$, and $C_5$); linear or branched alkanal, in particular lower alkanal ($C_1$, $C_2$, $C_3$, $C_4$, and $C_5$, e.g. COH, $CH_2COH$, $CH_2CH_2COH$; linear or branched alkyl carboxyl group, in particular lower alkyl carboxyl group ($C_1$, $C_2$, $C_3$, $C_4$ and $C_5$, e.g. formic, acetic, propionic, butyric, pentanoic acid group); substituted linear or branched alkyl carboxyl groups, in particular lower alkyl carboxyl group ($C_2$, $C_3$, $C_4$ and $C_5$, e.g. 2-methyl acetic acid, acetic acid, propionic acid, butyric acid, pentanoic acid group); aryl, in particular phenyl; substituted aryl, in particular substituted aryl; heteroaryl; substituted heteroaryl; alkylaryl, in particular benzyl; substituted alkylaryl; in particular substituted benzyl; alkylheteroaryl; substituted alkylheteroaryl; aminoalkyl, $C_1$, $C_2$, $C_3$, $C_4$ and $C_5$, e.g. —$NHCH_3$, —$NHCH_2CH3$, —$N(CH_3)_2$; substituted aminoalkyl; aminoketone, in particular —$NHCOCH_3$; substituted aminoketone; aminoaryl, in particular —NH-Ph; substituted aminoaryl, in particular substituted —NH-Ph; CN; $NH_2$; Halogen, in particular F, Cl, and Br; $NO_2$; OH; SH; NH; CN; or COOH group.

The following figures and examples are merely illustrative of the present invention and should not be construed to limit the scope of the invention as indicated by the appended claims in any way.

BRIEF DESCRIPTION OF THE TABLES AND FIGURES

The patent or application file contains at least one drawing executed in color. Copies of this patent or patent application publication, with color drawing(s), will be provided by the Office upon request and payment of the necessary fee.

Table 1: Response of hTAS2R1 to chloramphenicol, humulone, diphenylthiourea, picrotoxinin and yohimbine.
Table 2 Response of hTAS2R3 to creatinine.
Table 3 Response of hTAS2R7 to creatinine and cromolyn.
Table 4 Response of hTAS2R40 to humulone.

FIGS. 1A-1D Expression and cell surface localisation of hTAS2R1 (FIG. 1A), hTASR3 (FIG. 1B), hTASR7 (FIG. 1C) and hTASR40 (FIG. 1D) in HEK 293 cells. Indirect immunocytochemistry of the TAS2R receptors (shown in light grey) using monoclonal anti-HSV antibody (Novagen) and secondary anti-mouse IgG antibody coupled to Alexa488 (Molecular Probes). Cells membrane (shown in dark grey) was stained with Avidin-D-Texas-Red. Yellow colour shows the colocalisation of the receptor with the cell surface.

Figure 2A:
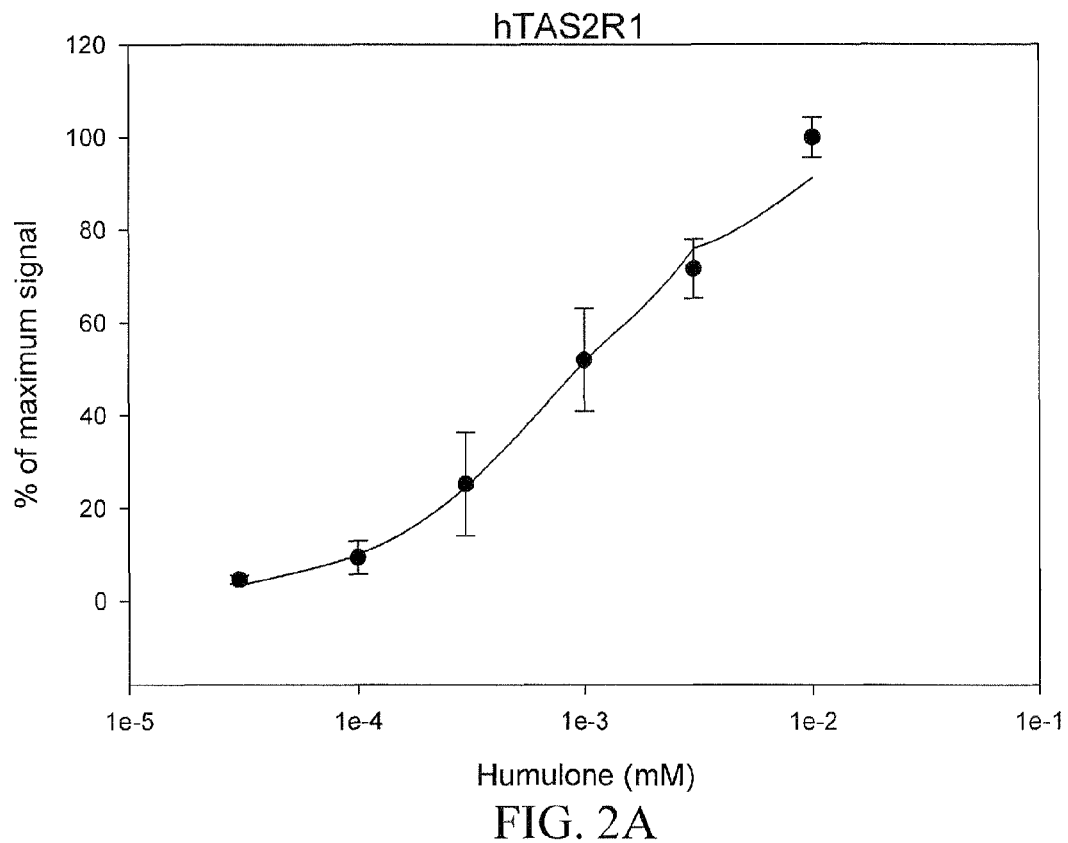
Figure 2B:
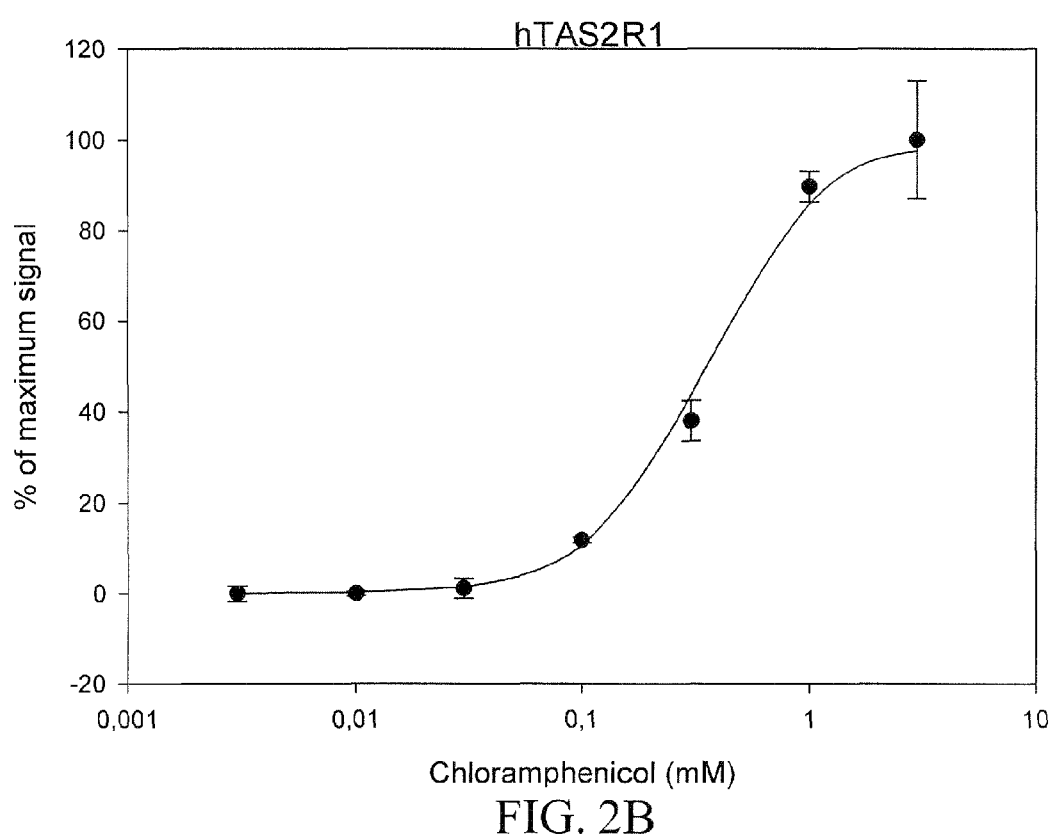

FIGS. 2A-2B Dose-response curves of hTAS2R1 for humulone and chloramphenicol. Different concentrations of humulone (FIG. 2A) and chloramphenicol (FIG. 2B) were applied onto hTAS2R1 transfected cells.

Figure 3:
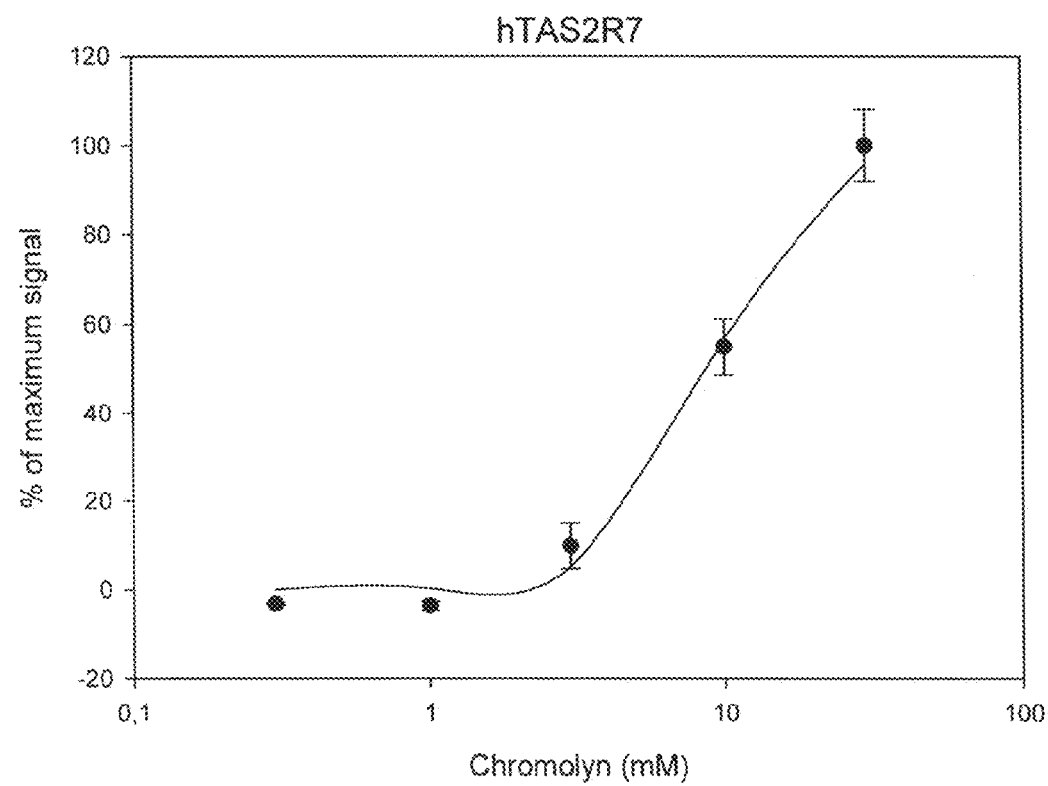

FIG. 3 Dose-response curves of hTAS2R7 for cromolyn. Different concentrations of cromolyn were applied onto hTAS2R7 transfected cells.

EXAMPLES

Conditional Expression of hTAS2R1, hTASR3, hTASR7 and hTASR40

Ligand screening using an automated fluorometric imaging plate reader (Molecular Devices) was essentially done as described (Bufe B. et al. (2002) Nature Genetics 32: 397-401). Briefly: The cells were seeded at a density of 70,000±10,000 cells per well in 96-well microtiter plates. The cDNA of hTAS2R1, hTASR3, hTASR7 and hTASR40 supplemented with an amino terminal export tag corresponding to amino acids 1-45 of rat somatostatin receptor 3 and a carboxy terminal HSV-tag was transiently transfected into HEK-293T cells stably expressing the chimeric G-protein subunit $G_{\alpha 16gust44}$ (Ueda T. et al. (2003) J. Neurosci. 23: 7376-7380) using Lipofectamine 2000 (Invitrogen). Expression rates were determined to be 20% for hTAS2R1; 35% for hTAS2R3, 14% for hTAS2R7 and 29% for hTAS2R40 by indirect immunocyclochemistry using monoclonal anti-HSV antibodies (Novagen) and secondary anti-mouse IgG antibodies coupled to Alexa 488 (Molecular probes) see (FIG. 1). 24-32 hours after transfection, the cells were then loaded for 1 hour with the calcium sensitive dye Fluo4-AM (2 µg/ml in DMEM, Molecular Probes). Cells were washed 3× in solution C1 (130 mM NaCl, 5 mM KCl, 10 mM Hepes, 2 mM $CaCl_2$, and 10 mM Glucose, pH 7,4). Calcium mobilization was monitored by an automated fluorometric imaging plate reader (Molecular Devices). Ligands (Sigma-Aldrich) were dissolved in C1 solution. All data were collected from experiments carried out in triplicate. For dose-response curves, the obtained calcium signals were corrected for and normalized to background fluorescence $\Delta F/F=(F-F_0)/F_0$ and baseline noise was subtracted. Results for the respective hTAS2Rs are shown in Table 1 through 4 below.

TABLE 1

Response of hTAS2R1 on chloramphenicol, humulone, diphenylthiourea, picrotoxinin and yohimbine

| compound | structure | mock | signal | concentration (mM) | threshold (mM) | $ED_{50}$ (mM) | max amplitude (counts) |
|---|---|---|---|---|---|---|---|
| Chloramphenicol | 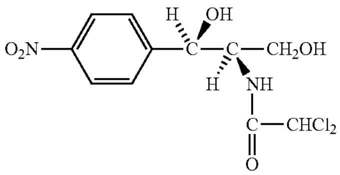 | | | 1<br>0.3<br>0.1<br>0.03 | ~0.1 | 0.2 | 9000 |
| Humulone | 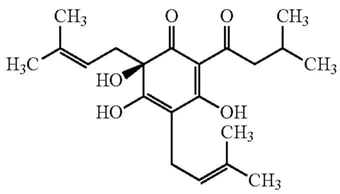 | | | 0.0003<br>0.0001<br>0.00003 | ~0.0001 | 0.0009 | 9000 |
| Diphenylthiourea | 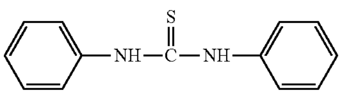 | | | 1.0<br>0.3<br>0.1<br>0.03 | ~0.1 | — | 4000 |
| Picrotoxinin | 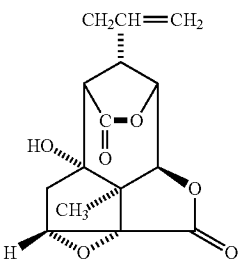 | | | 0.001<br>0.0001<br>0.000001 | ~0.0001 | no data | 2000 |
| Yohimbine | 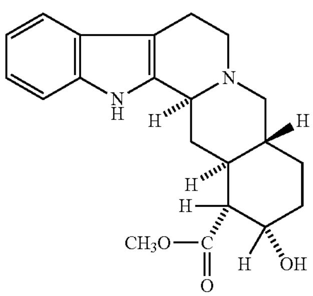 | | | 0.1<br>0.03<br>0.01 | ~0.03 | no data | 3000 |

Scale denotes 1 min and 2000 counts.

TABLE 2

Response of hTAS2R3 on creatinine

| compound | structure | mock | signal | concentration (mM) | threshold (mM) | $ED_{50}$ (mM) | max. amplitude (counts) |
|---|---|---|---|---|---|---|---|
| Creatinine | 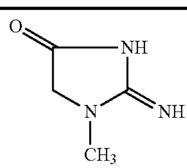 | | | 150<br>100<br>30 | ~30 | not determ. | 5000 |

Scale denotes 1 min and 1000 counts.

TABLE 3

Response of hTAS2R7 on creatinine and cromolyn

| compound | structure | mock | signal | concentration (mM) | threshold (mM) | ED$_{50}$ (mM) | max. amplitude (counts) |
|---|---|---|---|---|---|---|---|
| Creatinine | 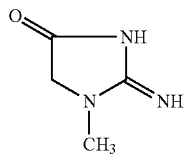 | | | 150<br>100<br>30 | ~10 | not determ. | 3000 |
| Cromolyn | 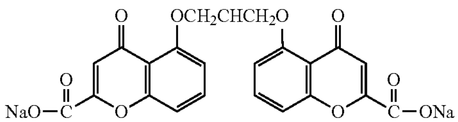 | | | 30<br>10<br>3<br>1 | ~1 | 9 | 3000 |

Scale denotes 1 min and 1000 counts.

TABLE 4

Response of hTAS2R40 on humulone

| compound | structure | mock | signal | concentration (mM) | threshold (mM) | ED$_{50}$ (mM) | max. amplitude (counts) |
|---|---|---|---|---|---|---|---|
| Humulone | 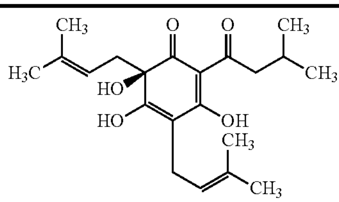 | | | 0.0001<br>0.00001<br>0.00003 | <0.00003 | not determ. | 6000 |

Scale denotes 1 min and 2000 counts.

We claim:

1. A method for isolating an agonist or antagonist of bitter taste receptor activity comprising:
 (a) contacting:
 (i) a polypeptide with a potential antagonist; or
 (ii) a cell expressing a polypeptide with a potential antagonist;
 wherein said polypeptide according to (i) or (ii) has bitter taste receptor activity and wherein said polypeptide according to (i) or (ii):
 (1) comprises SEQ ID NO: 4; or
 (2) comprises a polypeptide containing only conservative amino acid substitutions in the amino acid sequence of SEQ ID NO: 4, said conservative amino acid substitutions numbering 15 or fewer conservative amino acid substitutions in the amino acid sequence of SEQ ID NO: 4; and
 (b) determining whether the potential antagonist antagonizes the bitter taste receptor activity of said polypeptide;
 wherein prior, concomitantly and/or after step (a) said polypeptide according to (i) or said cell according to (ii) is contacted with an agonist selected from the group consisting of chloramphenicol, humulone, diphenylthiourea, picrotoxinin and agonistic derivatives thereof.

2. The method of claim 1, further comprising admixing the identified antagonist with foodstuffs or any precursor material or additive employed in the production of foodstuffs.

3. The method of claim 1, further comprising formulating the antagonist with an active agent in a pharmaceutically acceptable form.

4. The method according to claim 1, wherein said polypeptide comprises SEQ ID NO: 4 and said polypeptide has bitter taste receptor activity.

5. The method according to claim 1, wherein said method comprises contacting a cell expressing a polypeptide comprising SEQ ID NO: 4, said polypeptide having bitter taste receptor activity.

6. The method according to claim 1, wherein said method comprises contacting a cell expressing a polypeptide containing only conservative amino acid substitutions in the amino acid sequence of SEQ ID NO: 4, said conservative amino acid substitutions numbering 15 or fewer conservative amino acid substitutions in the amino acid sequence of SEQ ID NO: 4.

7. The method according to claim 1, wherein said method comprises contacting a cell expressing a polypeptide containing only conservative amino acid substitutions in the amino acid sequence of SEQ ID NO: 4, said conservative amino acid substitutions numbering 14 or fewer conservative amino acid substitutions in the amino acid sequence of SEQ ID NO: 4.

8. The method according to claim 1, wherein said method comprises contacting a cell expressing a polypeptide containing only conservative amino acid substitutions in the amino acid sequence of SEQ ID NO: 4, said conservative amino acid substitutions numbering 10 or fewer conservative amino acid substitutions in the amino acid sequence of SEQ ID NO: 4.

9. The method according to claim 1, wherein said method comprises contacting a cell expressing a polypeptide containing only conservative amino acid substitutions in the amino acid sequence of SEQ ID NO: 4, said conservative amino acid substitutions numbering 8 or fewer conservative amino acid substitutions in the amino acid sequence of SEQ ID NO: 4.

10. The method according to claim 1, wherein said method comprises contacting a cell expressing a polypeptide containing only conservative amino acid substitutions in the amino acid sequence of SEQ ID NO: 4, said conservative amino acid substitutions numbering 5 or fewer conservative amino acid substitutions in the amino acid sequence of SEQ ID NO: 4.

11. The method according to claim 1, wherein said method comprises contacting a cell expressing a polypeptide containing only conservative amino acid substitutions in the amino acid sequence of SEQ ID NO: 4, said conservative amino acid substitutions numbering 3 or fewer conservative amino acid substitutions in the amino acid sequence of SEQ ID NO: 4.

12. The method according to claim 1, wherein said method comprises contacting a polypeptide containing only conservative amino acid substitutions in the amino acid sequence of SEQ ID NO: 4, said conservative amino acid substitutions numbering 15 or fewer conservative amino acid substitutions in the amino acid sequence of SEQ ID NO: 4.

13. The method according to claim 1, wherein said method comprises contacting a polypeptide containing only conservative amino acid substitutions in the amino acid sequence of SEQ ID NO: 4, said conservative amino acid substitutions numbering 14 or fewer conservative amino acid substitutions in the amino acid sequence of SEQ ID NO: 4.

14. The method according to claim 1, wherein said method comprises contacting a polypeptide containing only conservative amino acid substitutions in the amino acid sequence of SEQ ID NO: 4, said conservative amino acid substitutions numbering 10 or fewer conservative amino acid substitutions in the amino acid sequence of SEQ ID NO: 4.

15. The method according to claim 1, wherein said method comprises contacting a polypeptide containing only conservative amino acid substitutions in the amino acid sequence of SEQ ID NO: 4, said conservative amino acid substitutions numbering 8 or fewer conservative amino acid substitutions in the amino acid sequence of SEQ ID NO: 4.

16. The method according to claim 1, wherein said method comprises contacting a polypeptide containing only conservative amino acid substitutions in the amino acid sequence of SEQ ID NO: 4, said conservative amino acid substitutions numbering 5 or fewer conservative amino acid substitutions in the amino acid sequence of SEQ ID NO: 4.

17. The method according to claim 1, wherein said method comprises contacting a polypeptide containing only conservative amino acid substitutions in the amino acid sequence of SEQ ID NO: 4, said conservative amino acid substitutions numbering 3 or fewer conservative amino acid substitutions in the amino acid sequence of SEQ ID NO: 4.

* * * * *

UNITED STATES PATENT AND TRADEMARK OFFICE
CERTIFICATE OF CORRECTION

PATENT NO. : 8,012,701 B2
APPLICATION NO. : 12/890897
DATED : September 6, 2011
INVENTOR(S) : Bernd Bufe et al.

It is certified that error appears in the above-identified patent and that said Letters Patent is hereby corrected as shown below:

Column 17,
Line 28, Row "Picrotoxinin"

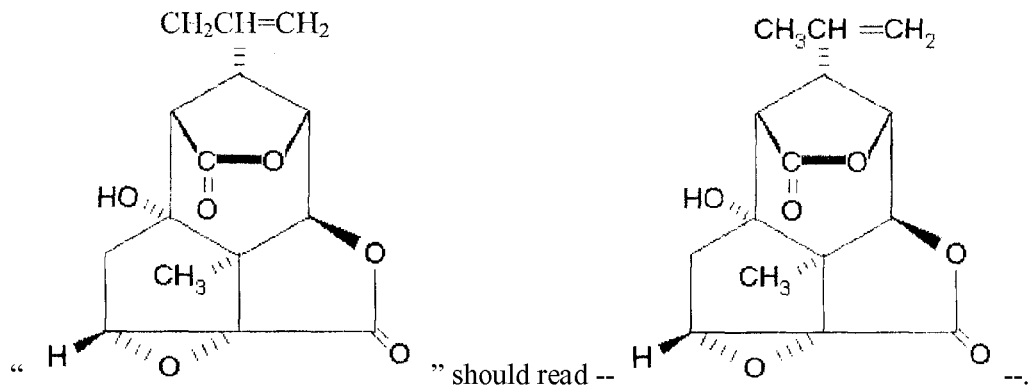

Column 19,
Line 16, Row "Cromolyn"

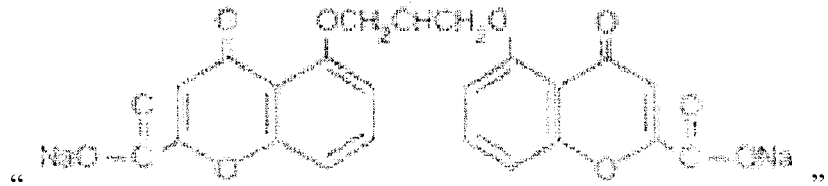

should read

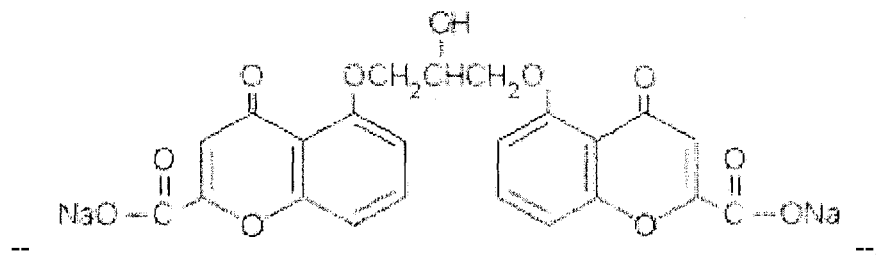

Signed and Sealed this
Seventh Day of February, 2012

David J. Kappos
*Director of the United States Patent and Trademark Office*

SEQUENCE LISTING

<160> NUMBER OF SEQ ID NOS: 8

<210> SEQ ID NO 1
<211> LENGTH: 897
<212> TYPE: DNA
<213> ORGANISM: Homo sapiens

<400> SEQUENCE: 1

```
atgctagagt ctcacctcat tatctatttt cttcttgcag tgatacaatt tcttcttggg      60
attttcacaa atggcatcat tgtggtggtg aatggcattg acttgatcaa gcacagaaaa     120
atggctccgc tggatctcct tctttcttgt ctggcagttt ctagaatttt tctgcagttg     180
ttcatcttct acgttaatgt gattgttatc ttcttcatag aattcatcat gtgttctgcg     240
aattgtgcaa ttctcttatt tataaatgaa ttggaacttt ggcttgccac atggctcggc     300
gttttctatt gtgccaaggt tgccagcgtc cgtcacccac tcttcatctg gttgaagatg     360
aggatatcca agctggtccc atggatgatc ctggggtctc tgctatatgt atctatgatt     420
tgtgttttcc atagcaaata tgcagggttt atggtcccat acttcctaag gaaatttttc     480
tcccaaaatg ccacaattca aaaagaagat acactggcta tacagatttt ctcttttgtt     540
```

```
gctgagttct cagtgccatt gcttatcttc cttttgctg ttttgctctt gatttctct      600 ctggggaggc acaccggca atgagaaac acagtggccg gcagcagggt tcctggcagg      660
ggtgcaccca tcagcgcgtt gctgtctatc ctgtccttcc tgatcctcta cttctcccac    720
tgcatgataa agttttct ctcttctcta agtttcaca tcagaaggtt catctttctg      780
ttcttcatcc ttgtgattgg tatatacccct tctggacact ctctcatctt aattttagga   840
aatcctaaat tgaaacaaaa tgcaaaaaag ttcctcctcc acagtaagtg ctgtcag       897
```

```
<210> SEQ ID NO 2
<211> LENGTH: 299
<212> TYPE: PRT
<213> ORGANISM: Homo sapiens

<400> SEQUENCE: 2

Met Leu Glu Ser His Leu Ile Ile Tyr Phe Leu Leu Ala Val Ile Gln
1               5                   10                  15

Phe Leu Leu Gly Ile Phe Thr Asn Gly Ile Val Val Asn Gly
            20                  25                  30

Ile Asp Leu Ile Lys His Arg Lys Met Ala Pro Leu Asp Leu Leu Leu
        35                  40                  45

Ser Cys Leu Ala Val Ser Arg Ile Phe Leu Gln Leu Phe Ile Phe Tyr
    50                  55                  60

Val Asn Val Ile Val Ile Phe Phe Ile Glu Phe Ile Met Cys Ser Ala
65                  70                  75                  80

Asn Cys Ala Ile Leu Leu Phe Ile Asn Glu Leu Glu Leu Trp Leu Ala
                85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
        115                 120                 125

Met Ile Leu Gly Ser Leu Leu Tyr Val Ser Met Ile Cys Val Phe His
    130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
    210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Leu Lys Phe His Ile Arg Arg
                245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
        275                 280                 285

Lys Lys Phe Leu Leu His Ser Lys Cys Cys Gln
    290                 295

<210> SEQ ID NO 3
<211> LENGTH: 948
```

```
<212> TYPE: DNA
<213> ORGANISM: Homo sapiens

<400> SEQUENCE: 3
atgatgggac tcaccgaggg ggtgttcctg attctgtctg gcactcagtt cacactggga      60
attctggtca attgtttcat tgagttggtc aatggtagca gctggttcaa gaccaagaga     120
atgtctttgt ctgacttcat catcaccacc ctggcactct tgaggatcat tctgctgtgt     180
attatcttga ctgatagttt tttaatagaa ttctctccca acacacatga ttcagggata     240
ataatgcaaa ttattgatgt ttcctggaca tttacaaacc atctgagcat ttggcttgcc     300
acctgtcttg gtgtcctcta ctgcctgaaa atcgccagtt tctctcaccc cacattcctc     360
tggctcaagt ggagagtttc tagggtgatg gtatggatgc tgttgggtgc actgctctta     420
tcctgtggta gtaccgcatc tctgatcaat gagtttaagc tctattctgt ctttagggga     480
attgaggcca ccaggaatgt gactgaacac ttcagaaaga agaggagtga gtattatctg     540
atccatgttc tgggactct gtggtacctg cctcccttaa ttgtgtccct ggcctcctac      600
tctttgctca tcttctccct ggggaggcac acacggcaga tgctgcaaaa tgggacaagc     660
tccagagatc caaccactga ggcccacaag agggccatca gaatcatcct ttccttcttc     720
tttctcttct tactttactt tcttgctttc ttaattgcat catttggtaa tttcctacca     780
aaaaccaaga tggctaagat gattggcgaa gtaatgacaa tgttttatcc tgctggccac     840
tcatttattc tcattctggg gaacagtaag ctgaagcaga catttgtagt gatgctccgg     900
tgtgagtctg gtcatctgaa gcctggatcc aagggaccca ttttctctct                948

<210> SEQ ID NO 4
<211> LENGTH: 316
<212> TYPE: PRT
<213> ORGANISM: Homo sapiens

<400> SEQUENCE: 4

Met Met Gly Leu Thr Glu Gly Val Phe Leu Ile Leu Ser Gly Thr Gln
1               5                   10                  15

Phe Thr Leu Gly Ile Leu Val Asn Cys Phe Ile Glu Leu Val Asn Gly
            20                  25                  30

Ser Ser Trp Phe Lys Thr Lys Arg Met Ser Leu Ser Asp Phe Ile Ile
        35                  40                  45

Thr Thr Leu Ala Leu Leu Arg Ile Ile Leu Leu Cys Ile Ile Leu Thr
    50                  55                  60

Asp Ser Phe Leu Ile Glu Phe Ser Pro Asn Thr His Asp Ser Gly Ile
65                  70                  75                  80

Ile Met Gln Ile Ile Asp Val Ser Trp Thr Phe Thr Asn His Leu Ser
                85                  90                  95

Ile Trp Leu Ala Thr Cys Leu Gly Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Val Met Val Trp Met Leu Leu Gly Ala Leu Leu Ser Cys Gly Ser
    130                 135                 140

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
                165                 170                 175

Glu Tyr Tyr Leu Ile His Val Leu Gly Thr Leu Trp Tyr Leu Pro Pro
            180                 185                 190
```

```
Leu Ile Val Ser Leu Ala Ser Tyr Ser Leu Ile Phe Ser Leu Gly
        195                 200                 205

Arg His Thr Arg Gln Met Leu Gln Asn Gly Thr Ser Arg Asp Pro
210                 215                 220

Thr Thr Glu Ala His Lys Arg Ala Ile Arg Ile Leu Ser Phe Phe
225                 230                 235                 240

Phe Leu Phe Leu Leu Tyr Phe Leu Ala Phe Leu Ile Ala Ser Phe Gly
            245                 250                 255

Asn Phe Leu Pro Lys Thr Lys Met Ala Lys Met Ile Gly Glu Val Met
                260                 265                 270

Thr Met Phe Tyr Pro Ala Gly His Ser Phe Ile Leu Ile Leu Gly Asn
            275                 280                 285

Ser Lys Leu Lys Gln Thr Phe Val Val Met Leu Arg Cys Glu Ser Gly
        290                 295                 300

His Leu Lys Pro Gly Ser Lys Gly Pro Ile Phe Ser
305                 310                 315
```

<210> SEQ ID NO 5
<211> LENGTH: 957
<212> TYPE: DNA
<213> ORGANISM: Homo Sapiens

<400> SEQUENCE: 5

```
atggcagata aagtgcagac tactttattg ttcttagcag ttggagagtt ttcagtgggg    60
atcttaggga tgcattcat tggattggta aactgcatgg actgggtcaa gaagaggaaa   120
attgcctcca ttgatttaat cctcacaagt ctggccatat ccagaatttg tctattgtgc   180
gtaatactat tagattgttt tatattggtg ctatatccag atgtctatgc cactggtaaa   240
gaaatgagaa tcattgactt cttctggaca ctaaccaatc atttaagtat ctggtttgca   300
acctgcctca gcattactac ttcttcaag ataggtaatt tctttcaccc acttttcctc   360
tggatgaagt ggagaattga cagggtgatt cctggattc tactggggtg cgtggttctc   420
tctgtgttta ttagccttcc agccactgag aatttgaacg ctgatttcag gttttgtgtg   480
aaggcaaaga ggaaaacaaa cttaacttgg agttgcagag taaataaaac tcaacatgct   540
tctaccaagt atttctcaa cctggcaacg ctgctcccct tttgtgtgtg cctaatgtcc   600
tttttcctct tgatcctctc cctgcggaga catatcaggc gaatgcagct cagtgccaca   660
gggtgcagag accccagcac agaagcccat gtgagagccc tgaaagctgt catttccttc   720
cttctcctct ttattgccta ctatttgtcc tttctcattg ccacctccag ctactttatg   780
ccagagacgg aattagctgt gatttttggt gagtccatag ctctaatcta ccctcaagt   840
cattcattta tcctaatact ggggaacaat aaattaagac atgcatctct aaaggtgatt   900
tggaaagtaa tgtctattct aaaaggaaga aaattccaac aacataaaca aatctga     957
```

<210> SEQ ID NO 6
<211> LENGTH: 318
<212> TYPE: PRT
<213> ORGANISM: Homo sapiens

<400> SEQUENCE: 6

```
Met Ala Asp Lys Val Gln Thr Thr Leu Leu Phe Leu Ala Val Gly Glu
1               5                   10                  15

Phe Ser Val Gly Ile Leu Gly Asn Ala Phe Ile Gly Leu Val Asn Cys
            20                  25                  30

Met Asp Trp Val Lys Lys Arg Lys Ile Ala Ser Ile Asp Leu Ile Leu
```

```
                        35                  40                  45
Thr Ser Leu Ala Ile Ser Arg Ile Cys Leu Leu Cys Val Ile Leu Leu
 50                  55                  60

Asp Cys Phe Ile Leu Val Leu Tyr Pro Asp Val Tyr Ala Thr Gly Lys
 65                  70                  75                  80

Glu Met Arg Ile Ile Asp Phe Phe Trp Thr Leu Thr Asn His Leu Ser
                 85                  90                  95

Ile Trp Phe Ala Thr Cys Leu Ser Ile Tyr Tyr Phe Phe Lys Ile Gly
                100                 105                 110

Asn Phe His Pro Leu Phe Leu Trp Met Lys Trp Arg Ile Asp Arg
            115                 120                 125

Val Ile Ser Trp Ile Leu Leu Gly Cys Val Val Leu Ser Val Phe Ile
            130                 135                 140

Ser Leu Pro Ala Thr Glu Asn Leu Asn Ala Asp Phe Arg Phe Cys Val
145                 150                 155                 160

Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Phe Leu Leu Ile Leu Ser Leu
        195                 200                 205

Arg Arg His Ile Arg Arg Met Gln Leu Ser Ala Thr Gly Cys Arg Asp
    210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
        275                 280                 285

Asn Asn Lys Leu Arg His Ala Ser Leu Lys Val Ile Trp Lys Val Met
    290                 295                 300

Ser Ile Leu Lys Gly Arg Lys Phe Gln Gln His Lys Gln Ile
305                 310                 315
```

<210> SEQ ID NO 7
<211> LENGTH: 969
<212> TYPE: DNA
<213> ORGANISM: Homo sapiens

<400> SEQUENCE: 7

| | | | | | |
|---|---|---|---|---|---|
| atggcaacgg | tgaacacaga | tgccacagat | aaagacatat | ccaagttcaa | ggtcaccttc     60 |
| actttggtgg | tctccggaat | agagtgcatc | actggcatcc | ttgggagtgg | cttcatcacg    120 |
| gccatctatg | gggctgagtg | ggccaggggc | aaaacactcc | ccactggtga | ccgcattatg    180 |
| ttgatgctga | gcttttccag | gctcttgcta | cagatttgga | tgatgctgga | gaacattttc    240 |
| agtctgctat | tccgaattgt | ttataaccaa | aactcagtgt | atatcctctt | caaagtcatc    300 |
| actgtctttc | tgaaccattc | caatctctgg | tttgctgcct | ggctcaaagt | cttctattgt    360 |
| cttagaattg | caaacttcaa | tcatcctttg | ttcttcctga | tgaagaggaa | aatcatagtg    420 |
| ctgatgcctt | ggcttctcag | gctgtcagtg | ttggtttcct | taagcttcag | ctttcctctc    480 |
| tcgagagatg | tcttcaatgt | gtatgtgaat | agctccattc | ctatcccctc | ctccaactcc    540 |
| acggagaaga | agtacttctc | tgagaccaat | atggtcaacc | tggtattttt | ctataacatg    600 |

```
gggatcttcg ttcctctgat catgttcatc ctggcagcca ccctgctgat cctctctctc    660
aagagacaca ccctacacat gggaagcaat gccacagggt ccagggaccc cagcatgaag    720
gctcacatag ggccatcaa agccaccagc tactttctca tcctctacat tttcaatgca    780
attgctctat ttcttttccac gtccaacatc tttgacactt acagttcctg gaatattttg    840
tgcaagatca tcatggctgc ctaccctgcc ggccactcag tacaactgat cttgggcaac    900
cctgggctga aagagcctg gaagcggttt cagcaccaag ttcctcttta cctaaaaggg    960
cagactctg                                                             969
```

\<210\> SEQ ID NO 8
\<211\> LENGTH: 323
\<212\> TYPE: PRT
\<213\> ORGANISM: Homo sapiens

\<400\> SEQUENCE: 8

```
Met Ala Thr Val Asn Thr Asp Ala Thr Asp Lys Asp Ile Ser Lys Phe
 1               5                   10                  15

Lys Val Thr Phe Thr Leu Val Val Ser Gly Ile Glu Cys Ile Thr Gly
             20                  25                  30

Ile Leu Gly Ser Gly Phe Ile Thr Ala Ile Tyr Gly Ala Glu Trp Ala
         35                  40                  45

Arg Gly Lys Thr Leu Pro Thr Gly Asp Arg Ile Met Leu Met Leu Ser
     50                  55                  60

Phe Ser Arg Leu Leu Leu Gln Ile Trp Met Met Leu Glu Asn Ile Phe
 65                  70                  75                  80

Ser Leu Leu Phe Arg Ile Val Tyr Asn Gln Asn Ser Val Tyr Ile Leu
                 85                  90                  95

Phe Lys Val Ile Thr Val Phe Leu Asn His Ser Asn Leu Trp Phe Ala
            100                 105                 110

Ala Trp Leu Lys Val Phe Tyr Cys Leu Arg Ile Ala Asn Phe Asn His
        115                 120                 125

Pro Leu Phe Phe Leu Met Lys Arg Lys Ile Ile Val Leu Met Pro Trp
    130                 135                 140

Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ser Ile Pro Ile Pro
                165                 170                 175

Ser Ser Asn Ser Thr Glu Lys Lys Tyr Phe Ser Glu Thr Asn Met Val
            180                 185                 190

Asn Leu Val Phe Phe Tyr Asn Met Gly Ile Phe Val Pro Leu Ile Met
        195                 200                 205

Phe Ile Leu Ala Ala Thr Leu Leu Ile Leu Ser Leu Lys Arg His Thr
    210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
            260                 265                 270

Thr Tyr Ser Ser Trp Asn Ile Leu Cys Lys Ile Ile Met Ala Ala Tyr
        275                 280                 285

Pro Ala Gly His Ser Val Gln Leu Ile Leu Gly Asn Pro Gly Leu Arg
    290                 295                 300
```

-continued

```
Arg Ala Trp Lys Arg Phe Gln His Gln Val Pro Leu Tyr Leu Lys Gly
305                 310                 315                 320
Gln Thr Leu
```